United States Patent [19]
Branch

[11] Patent Number: 4,813,950
[45] Date of Patent: Mar. 21, 1989

[54] SANITARY MENSES PANTY

[76] Inventor: Wilma J. Branch, 2619 Arrowwood Trail, Ann Arbor, Mich. 48105

[21] Appl. No.: 907,323

[22] Filed: Sep. 15, 1986

[51] Int. Cl.$^4$ .............................................. A61F 13/16
[52] U.S. Cl. ........................................ 604/396; 2/401
[58] Field of Search .................... 604/394, 396; 2/401, 2/402; 428/315.5

[56] References Cited

U.S. PATENT DOCUMENTS

| | | | |
|---|---|---|---|
| 2,102,323 | 12/1937 | Kneibler | 2/401 |
| 2,636,494 | 4/1953 | Hon | 604/396 |
| 2,660,173 | 11/1953 | Erteszek | 604/394 |
| 2,706,389 | 4/1955 | Garrou et al. | 2/401 |
| 3,489,149 | 1/1970 | Larson | 604/394 |
| 3,595,732 | 7/1971 | Tingerthal | 428/315.5 |
| 3,613,686 | 10/1971 | De Woskin | 604/396 |
| 4,338,371 | 7/1982 | Dawn et al. | 604/375 |
| 4,347,844 | 9/1982 | Ohki et al. | 604/371 |
| 4,425,128 | 1/1984 | Motomura | 604/385.1 |
| 4,613,544 | 9/1986 | Burleigh | 428/315.5 |

FOREIGN PATENT DOCUMENTS 0127502 1/1929 Fed. Rep. of Germany ...... 604/396

Primary Examiner—C. Fred Rosenbaum
Assistant Examiner—Denise Whelton
Attorney, Agent, or Firm—James M. Deimen

[57] ABSTRACT

A washable reuseable sanitary panty designed to be worn during menses, normally occurring in non-pregnant women about every four weeks, from menarche to menopause. The sanitary panty is intended to be worn with a tampon or sanitary napkin to prevent leakage and soiling of outer garments. The panty comprises a highly elastic woven or knit fiber outer covering configured in the shape of a panty and a contiguous non-woven plastic film inner layer extending through the crotch, the inner layer being liquid water impermeable/water vapor permeable and of at least equal non-directional elasticity as the outer covering. In the preferred embodiment the panty is constructed of a spandex polyurethane fiber outer covering and a soft smooth microporous plastic film inner layer sewn to the outer layer. Both the outer and inner layer as well as the stitching are substantially unaffected by repeated washing and heated drying without the need for special care.

13 Claims, 1 Drawing Sheet

SANITARY MENSES PANTY

BACKGROUND OF THE INVENTION

The invention pertains to the field of women's lingerie and underwear and in particular to women's panties worn during menses. The field also includes other means for controlling the flow of fluids during menses and the absorption and control of fluid and solid waste from the body under conditions of incontinence or otherwise.

U.S. Pat. No. 4,044,769 discloses a women's panty having a fluid-type compartment for supporting a sanitary napkin therein and an opening on the inside of the compartment in the garment to receive fluid discharged from the body of the user. The panty is constructed of an elastic material with elastic legbands around the leg openings.

U.S. Pat. No. 4,205,679 discloses a multilayer disposable panty adapted for use by infants or incontinent adults and children. The inner and outer plies are constructed of a non-woven stretchable fabric which has been mechanically compressed to provide small pleats to thereby provide the desired stretch characteristics. Between the inner and outer plies is a liquid absorbent layer or panel.

U.S. Pat. No. 4,335,722 discloses a tampon having a super absorbent material as an inner core and a non-super absorbent cover surrounding the inner core. The non-super absorbent cover material suggested is rayon.

Another example of an incontinence panty is disclosed on page 29 of the Spring 1986 catalog of the National Wholesale Company of Lexington, N.C. The panty is disclosed as comprising spandex and nylon with a vinyl coated nylon panel.

U.S. Pats. Nos. 4,338,371 and 4,411,660 disclose a multilayer absorbent panty material and panty for use in contact with the skin to absorb fluids. The multilayer material includes multiple wicking layers and multiple absorbent materials. The multiple layers are covered by a single liquid impermeable/gas permeable layer overlaying the interwicking and absorbent layers. The liquid impermeable/gas permeable outside layer is disclosed as spandex made of a polyolefinic material for the purpose of preventing the passage of liquid but permitting the absorbent inner layers to breath. The multilayer absorbent materials form gels in the absorbent layers to retain urine and other liquid or semi-liquid materials. The multilayer absorbent material is quite clearly non-reusable and therefore any undergarment such as a panty formed therefrom would only be a disposable product. The material and undergarments formed therefrom are intended to be used by astronauts as a body waste collection means worn inside the spacesuit during extravehicular activity.

SUMMARY OF THE INVENTION

Applicant has developed the Sanitary Menses Panty disclosed below to provide an exceptionally comfortable garment that will prevent leakage of fluids during menses and attendant spoilage of outer garments. To provide comfort the outer layer of the panty is made of a soft tricot, spandex or other panty material which is partially or fully lined with a soft plastic film that comfortably flows and flexes with body movement. The particular soft film is a smooth non-woven material microporous in nature to prevent the passage of liquids but nevertheless permit the passage of gases such as water vapor. The soft film is very smooth and very elastic to stretch easily with the soft tricot or spandex.

In the preferred embodiment the soft film extends through the crotch area and above to the front and back. The soft film is stitched into place to the soft tricot or spandex outer layer and is at least as elastic as the soft tricot or spandex. The soft film, the stitching and the soft tricot or spandex are substantially unaffected with repeated washing and drying in a typical home washer and dryer combination. No special treatment or care is required beyond the usual care given to fine lingerie.

The smooth soft film inner layer is substantially more sanitary in use than cotton or other woven material and is more comfortable. In case of leakage from a tampon or sanitary napkin the film may be simply wiped clean to temporarily dry. Thus, the panty can be worn comfortably the entire day.

The panty can be worn by females of all age groups, from those entering menarche up to and through menopause. Although constructed primarily for menstruation, the panties can be worn for other purposes such as post-sexual activity to collect drainage and discharge from contraception and can be used to retain an absorbent pad for those who suffer from incontinence and other urinary tract problems. As a resuable item the new panty does not have to be purchased monthly and then discarded. The use of a gas permeable/liquid impermeable soft smooth single layer film through the crotch which can stretch in all directions with the outer layer allows the body to breath and be very comfortable yet prevents leakage or soilage from penetrating to outer garments. Because the film is very thin, very elastic and very soft the panties can be made very practical and appealing to the eye in a variety of styles and colors.

DESCRIPTION OF THE PREFERRED EMBODIMENT

Figure 1:
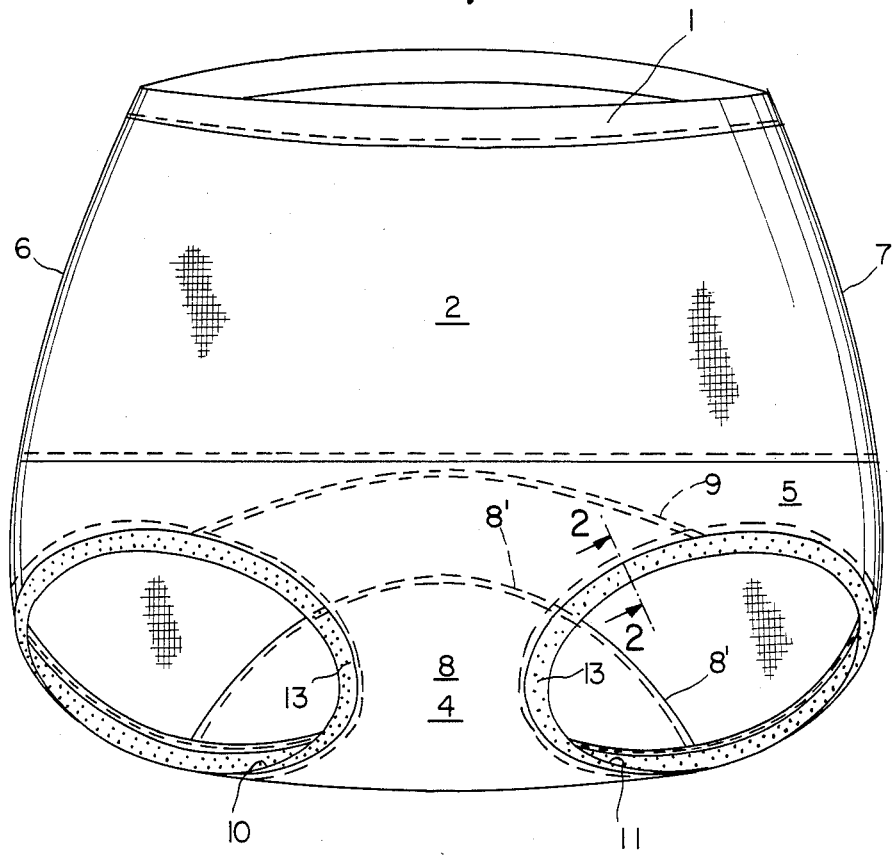
FIG. 1 illustrates a Sanitary Menses Panty according to the invention.

Illustrated in FIG. 1 is a front view of a women's panty constructed according to the invention. An elastic waistband 1 is sewn around the waist opening in the outer layer 5 of woven material from which the panty is generally constructed. A reinforced front support panel 2 is stitched to the outer layer to firmly control stomach bloat during menses. The reinforced front support panel 2 extends from the left side 6 of the panty to the right side 7 of the panty and is normally sewn in place. Optionally, the panel 2 may not extend fully to the sides 6 and 7. Although typically less elastic than the outer layer 5 of the panty, the reinforced front support panel is nevertheless sufficiently elastic to be worn comfortably. This reinforced front support panel is an optional item on the panty.

The outer layer of the panty is contructed of a woven or knit polyurethane, polyolefin, cotton or other fabric material to be highly elastic. Such materials are often known as tricot or spandex and used for a variety of products such as bathing suits and undergarments. The products are typically skin tight or almost skin tight and therefore to be comfortable, must accommodate and generally move with the skin of the wearer. The woven or knit fabric outer layer extends through the crotch area 4 of the panty.

On the inside of the panty within the crotch area 4 is an inner layer 8 of a nonwoven smooth plastic film. The inner layer plastic film is stitched about the periphery of the inner layer to the outer layer with clear plastic thread, extends inside the panty in front to about 1 to 2 inches above the crotch as indicated at 9 and extends in the back or seat area 8' to about 1 to 2 inches below the coccyx. The inner layer plastic film extends to both leg openings 10 and 11. A lace trim 13 surrounds each of the leg openings, 10 and 11.

Figure 2:
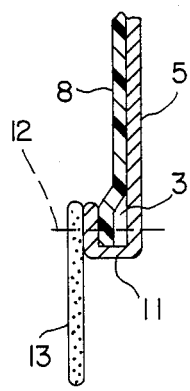
FIG. 2 illustrates a section through the inner film layer and outer woven layer of the panty.

As illustrated in FIG. 2 the outer layer 5 of a knit or woven material is lined in the crotch area with the non-woven plastic film 8 on the inside. At the leg opening 11 an elastic band 3 is stitched 12 between the plastic film 8 and the outer layer 5 with the outer layer 5 wrapped over. The high elasticity of the plastic film in combination with the elastic leg band stitched thereto prevent staining, soilage and leakage about the leg opening.

The plastic film comprises a very smooth and very elastic thin film having billions of micropores per square inch. The film is supplied as drawsheets under the Trademark "Tendercare" by Spenco Medical Corporation, Waco, Tex. The film permits the passage of gases such as water vapor therethrough but prevents the passage of liquid water or fluids such as blood and urine. The high elasticity of the film permits the film to stretch in any direction with the outer layer of spandex or other fiber. The washable nature of the film permits the panty constructed with the film to be washed repeatedly and dried in a dryer along with other fine washable undergarments. The Spenco film is also available from Deerfield Urethane, Inc., South Deerfield, Mass. as Dureflex (TM) product number PT 9300 and is a polyurethane film of 0.0018 inches thickness.

The Sanitary Menses Panty is intended to be worn with the conventional tampon or sanitary pad and is specifically designed to prevent inadvertent leakage onto other underwear or outerwear. If during the day the panty becomes soiled, the smooth plastic film can be easily wiped clean with a paper towel and the panty continued to be worn for the rest of the day. The film being breathable and at least as elastic as the outer fabric, is of a thickness on the order of 1 to 4 mils. The particular film supplied by Spenco as their Tendercare draw sheets product has been found to be far superior to other liquid impermeable/gas permeable plastic films.

I claim:

1. A substantially fluid non-absorbent repeatedly washable
   undergarment having a waist opening and leg openings comprising a highly elastic fiber outer covering extending over substantially the entire undergarment and a contiguous soft non-fiber microporous polyurethane film inner layer less than about 0.002 inches in thickness extending through the crotch and seat area of the undergarment,
   said non-fiber film being liquid water impermeable and water vapor permeable and of at least equal non-directional elasticity to the outer covering,
   said non-fiber film inner layer being stitched about the periphery thereof to the fiber outer covering to provide a permanent attachment, whereby the stitching, outer layer and inner layer are substantially unaffected by body fluids, water, permanent staining and heat thereby providing a repeatably washable and reuseable undergarment.

2. The undergarment of claim 1 wherein the waist and leg openings are trimmed with elastic bands, the leg bands being concealed between the film inner layer and the outer covering layer.

3. A repeatably washable undergarment having a waist
   opening and leg openings comprising a highly elastic fiber outer covering and a microporous polyurethane film inner layer contiguous thereto extending at least through the crotch and seat area of the undergarment,
   said film being less than about 0.002 inches in thickness,
   said film being liquid impermeable and vapor permeable, soft, non-fibrous and smooth with an elasticity substantially equal to or in in excess of the elasticity of the fiber outer covering, and
   said film inner layer being stitched about the periphery thereof to the fiber outer covering to provide a permanent attachment,
   whereby the stitching outer layer and inner layer are substantially unaffected by body fluids, water, permanent staining and heat thereby providing a repeatably washable and reuseable undergarment.

4. The undergarment of claim 3 including a front panel of less elasticity than the balance of the fiber outer covering.

5. The undergarment of claim 3 wherein the waist and leg openings are trimmed with elastic bands, the leg bands being concealed between the plastic film inner layer and the fiber outer covering about at least a portion of each leg opening.

6. The undergarment of claim 3 wherein the fiber outer
   covering layer is a polyurethane fiber.

7. The undergarment of claim 3 wherein the fiber outer covering layer is a polyolefin fiber.

8. The undergarment of claim 3 wherein the fiber outer covering layer is a woven tricot.

9. The undergarment of claim 3 wherein the fiber outer covering layer is a cotton fiber.

10. A repeatably washable undergarment having a waist opening and leg openings comprising a highly elastic fiber outer covering, a front support panel of substantially less elasticity than the elastic fiber outer covering and attached to the elastic fiber outer covering, said front support panel extending generally from above the leg openings and below the waist opening across the front of the undergarment, and a microporous polyurethane film inner layer less than about 0.002 inches in thickness contiguous to the outer covering extending at least through the crotch and seat area of the undergarment,
    said film being liquid impermeable and vapor permeable, soft, non-fibrous and smooth with an elasticity substantially equal to or in excess of the elasticity of the fiber outer covering, and
    said film inner layer being stitched about the periphery thereof to the fiber outer covering to provide a permanent attachment,
    whereby the stitching, outer layer and inner layer are substantially unaffected by body fluids, water, permanent staining and heat thereby providing a repeatable washable and reuseable undergarment.

11. The undergarment of claim 10 wherein the front support panel extends from one side of the undergarment to the other side and is stitched to the outer covering.

12. The undergarment of claim 10 wherein the waist and leg openings are trimmed with elastic bands, the leg bands being concealed between the plastic film inner layer and the fiber outer covering about at least a portion of each leg opening.

13. The undergarment of claim 10 wherein the fiber outer covering layer is a polyurethane fiber.

* * * * *